United States Patent [19]

Bowman

[11] Patent Number: 4,611,601
[45] Date of Patent: Sep. 16, 1986

[54] DISPOSABLE TRANSDUCER SYSTEMS

[75] Inventor: Ronald Bowman, Laguna Beach, Calif.

[73] Assignee: Transamerica Delaval Inc., Lawrenceville, N.J.

[21] Appl. No.: 581,481

[22] Filed: Feb. 17, 1984

[51] Int. Cl.⁴ ............................................. A61B 5/02
[52] U.S. Cl. .................................. 128/673; 128/748
[58] Field of Search .......................... 128/672–673, 128/675, 748, 6; 339/18 R, 18 C, 19

[56] References Cited

U.S. PATENT DOCUMENTS

| | | | |
|---|---|---|---|
| 3,831,588 | 8/1974 | Rindner | 128/675 |
| 3,894,535 | 7/1975 | Cannon et al. | 128/675 |
| 4,112,272 | 9/1978 | Jonsson et al. | 128/675 |
| 4,201,222 | 5/1980 | Haase | 128/675 |
| 4,232,373 | 11/1980 | Jackson et al. | 364/572 |
| 4,325,382 | 4/1982 | Miodownik | 128/675 |
| 4,407,298 | 10/1983 | Lentz et al. | 128/691 X |

Primary Examiner—Kyle L. Howell
Assistant Examiner—Angela D. Sykes
Attorney, Agent, or Firm—Benoit Law Corporation

[57] ABSTRACT

Methods and systems for operating a disposable transducer or other disposable apparatus, which may be subject to sterilization inimical to that disposable apparatus, determine parameters required for operation of the disposable apparatus and provide a record of that determined parameters on the disposable apparatus. These parameters are subsequently derived by machine-reading the record on the disposable apparatus in order to operate that disposable apparatus. The mentioned record may be made destructible by resterilization and the machine-reading and the operation of the disposable apparatus may be rendered impossible upon resterilization of that apparatus by destroying the mentioned record by said resterilization.

23 Claims, 5 Drawing Figures

DISPOSABLE TRANSDUCER SYSTEMS

BACKGROUND OF THE INVENTION

1. Field of the Invention

The subject invention relates to disposable transducer and other systems employing a disposable component having electrically adjustable or compensable parameters, and relates also to disposable transducer or other systems employing a component that may be exposed to sterilization inimical to such disposable component.

2. Information Disclosure Statement

The following disclosure statement is made pursuant to the duty of disclosure imposed by law and formulated in 37 CFR 1.56(a). No representation is hereby made that information thus disclosed in fact constitutes prior art, inasmuch as 37 CFR 1.56(a) relies on a materiality concept which depends on uncertain and inevitably subjective elements of substantial likelihood and reasonableness and inasmuch as a growing attitude appears to require citation of material which might lead to a discovery of pertinent material though not necessarily being of itself pertinent. Also, the following comments contain conclusions and observations which have only been drawn or become apparent after conception of the subject invention or which contrast the subject invention or its merits against the background of developments which may be subsequent in time or priority.

U.S. Pat. No. 3,831,588, by W. Rindner, issued Aug. 27, 1974, discloses a calibration system for a pressure sensing device wherein the pressure in the diaphragm chamber is varied by known amounts, thereby enabling calibration of the device in situ.

U.S. Pat. No. 3,894,535, by R. L. Cannon et al, issued July 15, 1975, discloses a blood pressure monitoring system with a manual control to compensate for the zero-offset of a pressure transducer when zero pressure is applied thereto.

U.S. Pat. No. 4,112,272, by S. E. Jonsson et al, issued Sept. 5, 1978, discloses an automatic zero balance and calibration mechanism controlled by a switch for a pressure converter device.

U.S. Pat. No. 4,232,373, by L. B. Jackson et al, issued Nov. 4, 1980, discloses a compensator system monitoring the response of a fluidic transducer and using that response to generate an error signal which controls the further filtering of the response in order to compensate for the portion of the response which is due to the transducer and not to the phenomena being measured, and also discloses various precalibration techniques from a variety of sources.

U.S. Pat. No. 4,325,382, by S. Miodownik, issued Apr. 20, 1982, proposes the use of a tunable active filter in the signal path between a transducer and a pressure indicator and adapts the frequency parameters of such filter to that of the catheter in real time, for various compensation purposes.

U.S. Pat. No. 4,201,222, by T. Haase, issued May 6, 1980, discloses an optical catheter using optical fibers for conducting light to and from an optical sensor, and employing a light modulator and optical multiplexer system for reading different parameters.

In a somewhat different vein, systems are known which indicate to an observer when a disposable apparatus or component has been sterilized for reuse. In this respect, there are stickers, labeled AMSCO, which have a blue stripe that turns black when exposed to sterilizing steam, and another stripe that assumes a rusty color when exposed to sterilizing ethylene oxide gas.

Despite a variety of proposals of this type, there persisted a need for technologically and economically disposable transducer and similar systems, as well as for safeguards against inimical effects of sterilization of components, and for improved calibration techniques and systems.

SUMMARY OF THE INVENTION

It is a general object of this invention to overcome the disadvantages and to meet the needs expressed or implicit in the above information disclosure statement or in other parts hereof.

It is a germane object of this invention to provide methods, means and apparatus for operating a disposable transducer or other apparatus.

It is a related object of this invention to provide disposable transducers or other apparatus with automatic compensation, balancing and other adjustments, involving preferably a machine-reading function.

It is a further object of this invention to prevent disposable transducers or other apparatus from being reused, after having been subjected to a resterilization process intended for reusable transducers or other apparatus.

Other objects of the invention will become apparent in the further course of this disclosure.

From one aspect thereof, the subject invention resides in methods, apparatus or systems for operating a disposable transducer or other apparatus subject to sterilization inimical to such disposable transducer or other apparatus. The invention according to this aspect resides, more specifically, in the improvement comprising, in combination, the steps of, or means for, determining parameters required for operation of the disposable transducer or other apparatus, providing a record of such determined parameters on the disposable transducer or other apparatus, deriving the above mentioned parameters by machine-reading in order to operate the disposable transducer or other apparatus, with the mentioned record being made destructible by resterilization, and the machine-reading and the operation of the disposable transducer or other apparatus being rendered impossible upon resterilization of the disposable transducer or other apparatus by destroying the mentioned record by its resterilization.

From another aspect thereof, the subject invention resides in methods, apparatus or systems for operating a disposable transducer or other apparatus including a transducing part and, more specifically, resides in the improvement comprising, in combination, the steps of or means for, determining parameters required for operation of the transducing part of the disposable transducer or other apparatus, providing a record of such determined parameters on the disposable transducer or other apparatus, machine-reading the parameters from such record, and operating the transducing part of the disposable transducer or other apparatus with the aid of the machine-read parameters.

From another aspect thereof, the subject invention resides in a disposable apparatus including a transducing part having parameters required for operation of that apparatus, comprising a machine-readable record of the parameters on the apparatus. According to a preferred embodiment of this aspect of the invention, wherein the disposable apparatus is subject to sterilization inimical to such disposable apparatus, the mentioned record is destructible by resterilization, thereby rendering a machine-reading and operation of the disposable apparatus impossible upon resterilization of the apparatus.

Other aspects of the invention will become apparent in the further course of this disclosure, and no limitation whatever is intended by all or any part of this summary in any respect.

BRIEF DESCRIPTION OF THE DRAWINGS

The subject invention and its various aspects and objects will become more readily apparent from the following detailed description of preferred embodiments thereof, illustrated by way of example in the accompanying drawings, in which like references designate like or functionally equivalent parts, and in which:

FIG. 5 is a front view of a transducer protected against resterilization while permitting initial sterilization prior to its first use.

DESCRIPTION OF PREFERRED EMBODIMENTS

Figure 1:
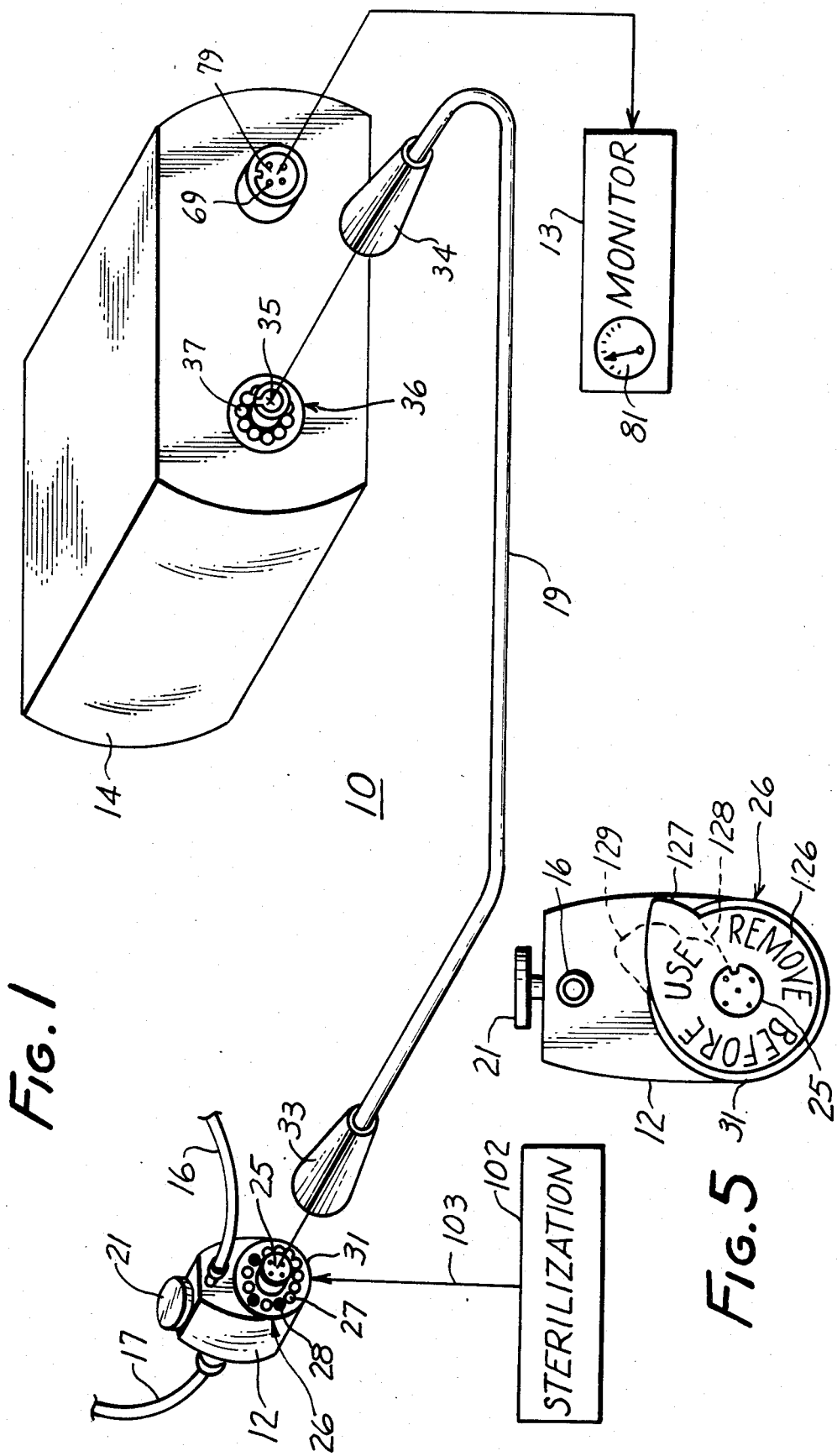
FIG. 1 is a partially perspective view of a transducer and transducer operating system according to an embodiment of the subject invention.

The transducer system 10 shown in FIG. 1 includes a transducer 12, a monitor 13 and a parameter setting and interfacing apparatus 14.

Figure 2:
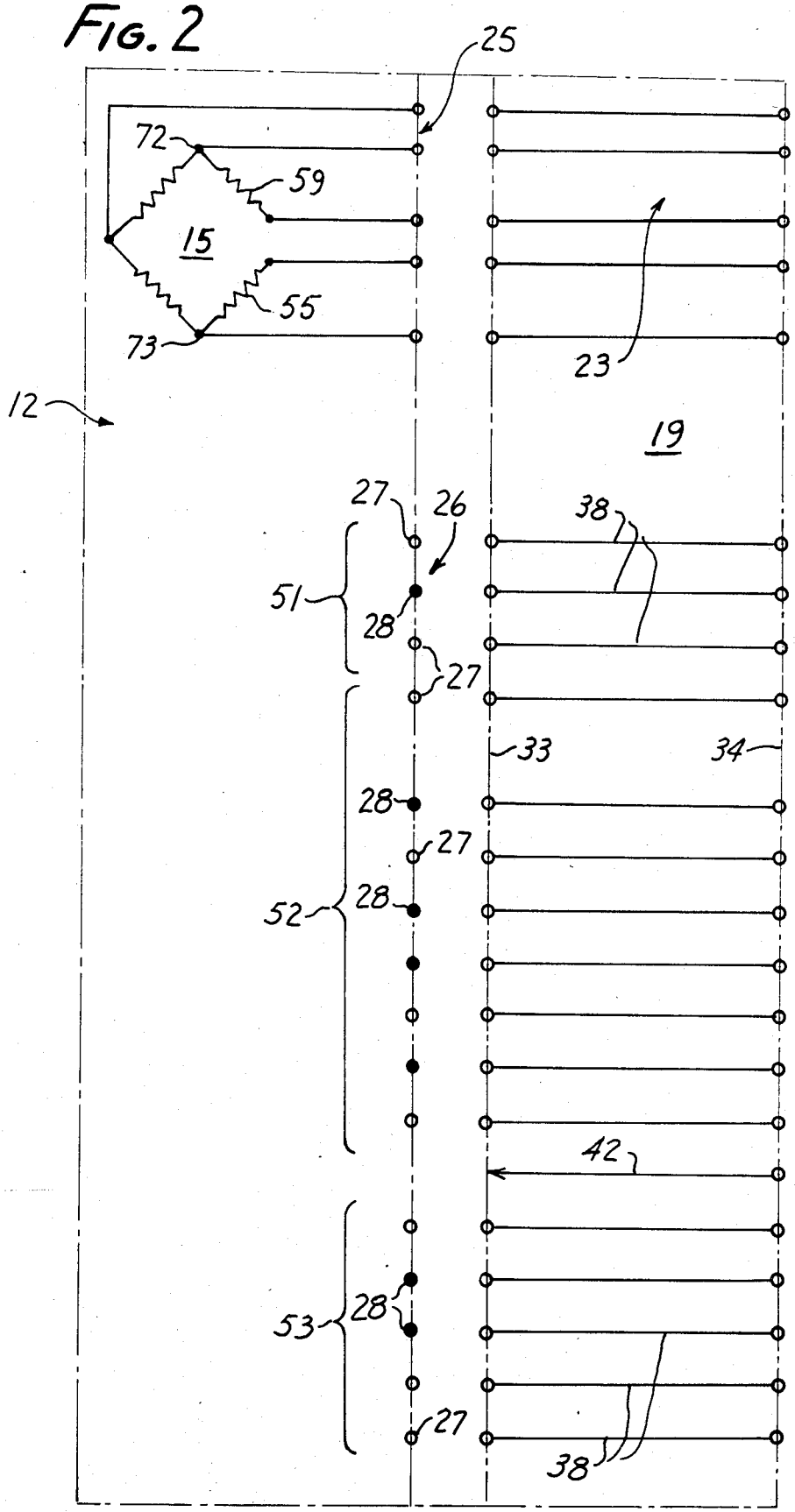
FIGS. 2 and 3, positioned side by side, are a circuit diagram of electrical and optical parts of the apparatus shown in FIG. 1, also according to an embodiment of the subject invention.

The transducer 12 may be of a conventional type, employing, for instance, a Wheatstone bridge 15, shown in FIG. 2, for transducing pressure or other received signals into corresponding electrical signals. By way of example, the transducer 12 may be a blood pressure transducer connected by a catheter 16 to a patient, living organism or other source of pressure pulses, and connected further by a line 17 to an infusion container or other source of liquid compatible with the living organism or other source of pressure signals. Transducer systems of this type are well known, having a diaphragm located at a dome or other chamber to which the catheter 16 and line 17 are connected. Pressure variations thus received correspondingly deflect the diaphragm, and such diaphragm deflections are sensed or otherwise transduced into electrical signals. In accordance with conventional practice, the resistive elements of the Wheatstone bridge 15 may be of the diffused silicon type, located on the diaphragm.

Transducers of this type are customarily and routinely used in hemodynamic or physiologic fluid pressure measuring or monitoring systems. In these and similar areas, there is a continuing need for a safe, maintenance-free transducer that will provide adequate data at very low cost. This, in turn, calls for an inexpensive transducer 12 that may be disposed of after a single use, at an overall cost lower than the overhead normally incurred in the resterilization and other handling procedures that have to be carried out with transducers of a more durable type.

Hemodynamic pressure transducers with disposable dome are satisfying this need only to some extent, requiring personnel to be capable of handling the dome replacement properly. Backdraws which have militated against replacing the transducer itself are the waste and expense incurred when a conventional transducer with its necessary temperature and sensitivity compensation and zero balancing elements is disposed of or thrown away.

For instance, conventional transducers need trimmable resistors connected in series and in parallel with the Wheatstone bridge and with parts of the arms thereof, in order to provide for the required zero balance, thermal zero and sensitivity compensations and span normalization. These elements add cost, as does their initial adjustment in the factory and, as necessary, in the field.

The subject invention, from the currently discussed aspect thereof, removes these elements and functions from the transducer 12, transferring them to the apparatus 12, with which the transducer is connected by a cable 19.

By way of example, the cable 19 may be of an electrical, optical or mixed electrical and optical type. In this or any other respect, the transducer 12 may be of the flow-flush type disclosed, for instance, in the copending U.S. Pat. application No. 06/483,207, filed Apr. 13, 1983, by Da Hong Le, for Catheter Flushing Systems, assigned to the common assignee hereof, and hereby incorporated by reference herein. Those flowflush devices have a manually depressable button or operator, shown at 21 in FIG. 1, for intermittently flushing the catheter 16 at a flushing flow rate higher than the seeping flow rate prevailing during operation of the transducer.

If flow-flush device and tranducer are integral as shown in FIG. 7 of that copending patent application, and the transducer is of an electrical type as shown therein, then the cable 19 may have an electrical portion 23 for transmitting electrical transducer signals from the Wheatstone bridge 15 to the interface 14 and hence to the monitor 13 and for effecting the requisite balancing, compensation and normalization operations electrically.

If desired, an optical pressure sensor may, however, be employed at 12. Reference may in this respect be had to the copending U.S. Pat. applications No. 06/468,446, filed Feb. 22, 1983 and 06/483,791, filed April 11, 1983 by John H. Jacobs for Evanescent Field Effect Apparatus and Methods and Pressure Transducer with Optical Output, respectively. Also, the above mentioned Haase Pat. No. 4,201,222, disclosing an optical sensor and fiber optics signal conduit, may be considered in this respect.

If such or any optical pressure sensor or transducer is employed, the cable portion 23 may at least partially be of an optical fiber type.

The transducer 12 has a connector 25, shown in FIGS. 1 and 2, for connection of the Wheatstone bridge 15 or other transducing part to the portion 23 of the cable 19. The transducer 12 also has a calibration/compensation code section 26, also shown in FIGS. 1 and 2, providing codes for operating the calibration/compensation portion of the apparatus 14.

By way of example, these codes may be provided by a variety of light-reflecting markings or spots 27 and light-absorbent markings or spots 28.

Techniques similar to laser trimming may be employed for providing the spots 27 and 28. In that case, a strip or disk 31 of photosensitive material may be employed at 26 for receiving luminous impressions generating the light absorbent dots 28 or, alternatively, the light-reflecting dots 27. In other words, a photographic technique may be employed for establishing the code 26 for the particular transducer 12 on which the alternative dots 27 and 28 are provided. In that case, the particular transducer 12 is preferably subjected to heat and pressure in an oven, whereby the Wheatstone bridge 15 provides output signals at 25 which are employed to determine the combinations of the code 26 necessary for the desired calibration and compensation during subsequent operation of the transducer. More on this is disclosed below in the context of FIG. 4.

For the moment, it is assumed that the code combination representative of the calibration and compensation needs of the particular transducer 12 has been established by any encoding technique at 26, and that the transducer is now ready for practical use. To this end, the cable 19 is attached to the connector 25 via a first terminal plug 33 covering also the code disk 31. The apparatus 14 then reads or senses the machine-readable code 26. To this end, the cable 19 has a second terminal plug 34 which corresponds to the first terminal plug 33 and which is attached to a connector 35 that corresponds to the connector 25 and which covers a cluster of photoreceptors 36 that correspond to the dots 27 and 28.

By way of example, the cluster 36 may contain photocells 37 for receiving light from the light-reflecting spots 27 via optical fibers 38 in the cable 19.

There are several known ways in which light can be transmitted from the code 26 to the photoreceptors 37. For instance, a light source 41 may be employed in the apparatus 14 for supplying the light needed to illuminate the code 26. An extra fiber 42 is shown in FIG. 2 for conveying light from the source 41 to the code 26, thereby illuminating the spots 27 and 28. In practice, there may be a fiber 42 for each of the fibers 38, whereby light from the source 41 is connected to each of the spots 27 and 28. Reference may in this respect also be had to the above mentioned Haase Pat. No. 4,201,222 showing a fiber optics cable for transmitting light and light stimuli to and from a monitor and related devices.

By way of example, the source 41 may be a laser, such as a diode laser for emitting coherent light for better readability of the code 26. If desired, a separate source may be employed for each spot 27 or 28 or for each fiber 38.

Figure 3:
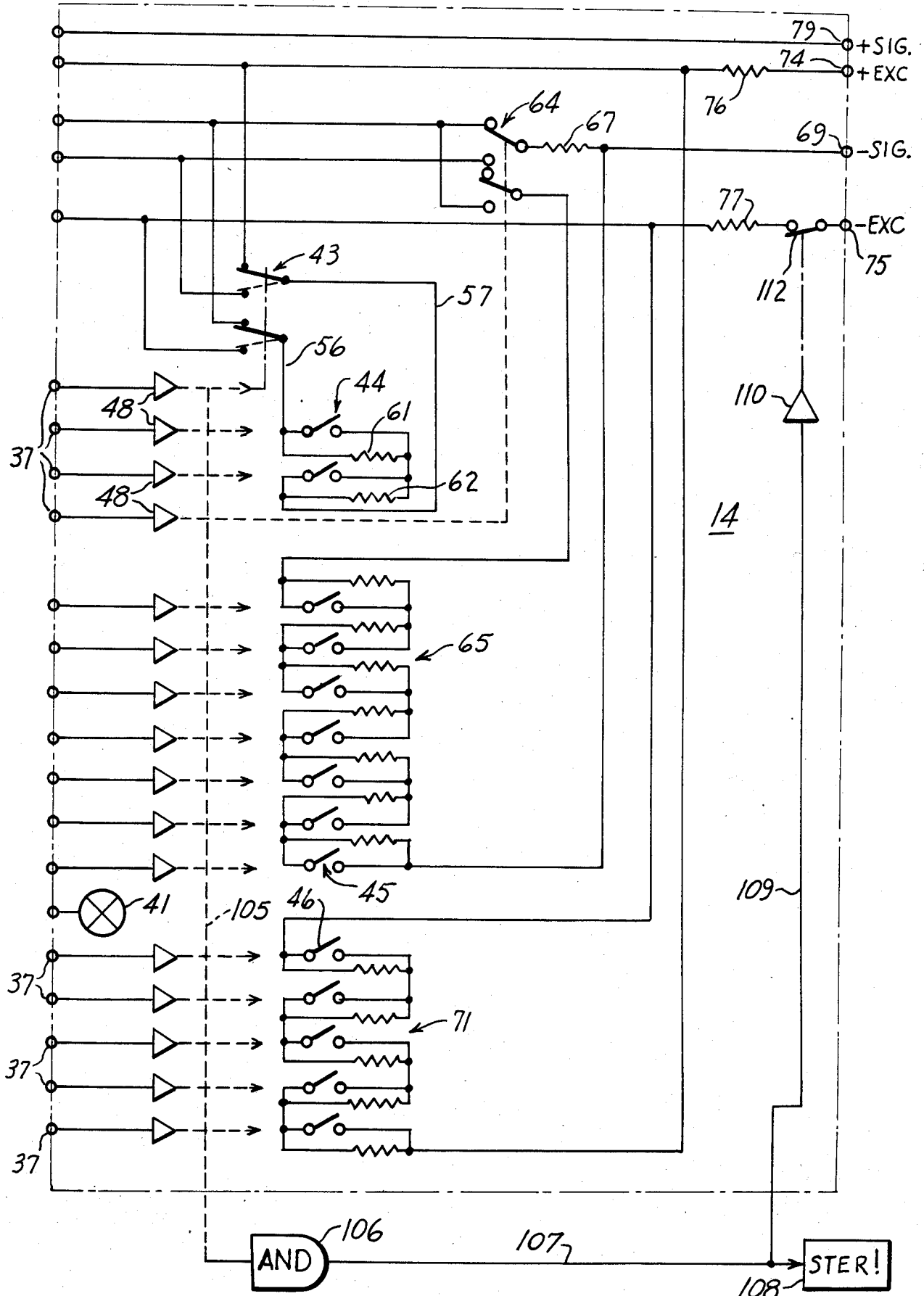

Switches or contacts 43, 44, 45 and 46 are shown in FIG. 3 for actuation in response to light received via fibers 38 from the code 26. In principle, these switches or contacts may be part of or actuated by relays. However, solid-state switches have the advantage of speed and simplicity, and operational amplifiers or drivers therefor are shown by triangular symbols 48 in FIG. 3.

In the illustrated embodiment shown in FIG. 2, the code is subdivided in a first cluster 51 of spots 27 and 28 for zero compensation, into a second cluster 52 for zero balancing, and into a third cluster 53 for sensitivity adjustment.

Since the top or first spot 27 in the first cluster 51 is light reflecting, the top or first driver 48 will be energized via the top or first fiber 38 and top or first photocell 37, whereby the switch 43 will be actuated to its second position indicated by dotted lines. In this manner, the Wheatstone bridge arm 55 will be connected via the cable section 23 to leads 56 and 57. Had the top spot of the cluster 51 been non-reflective, the switch 43 would have remained in its solidly illustrated position, and the leads 56 and 57 would have been connected to another Wheatstone bridge arm 59. Accordingly, a resistor 61 and/or a resistor 62 may be connected to either of the bridge arms 55 and 59, as determined by the light reflectivity of the top spot 27.

In the example shown in FIG. 2, the second spot 28 is non-reflective, so that the contact of the switch 44 in parallel to the resistor 61 remains open. On the other hand, the third spot 27 in the cluster 51 is light-reflective so that the contact of the switch 44 in parallel to the resistor 62 shunts that resistor. Accordingly, with the code cluster 51 as shown in FIG. 2, only the resistor 61 is connected in parallel with only the bridge arm 55. However, by appropriate variation of the code in the cluster 51, either the resistor 61 or the different resistors 62 or the resistors 61 and 62 in series can be connected in parallel to the bridge arms 55 or to the bridge arm 59, as required for a proper zero compensation of a given transducer 12 and Wheatstone bridge 15.

The same applies on an expanded scale with respect to the zero balancing effected by appropriate combination and variation of the spots 27 and 28 in the second cluster 52. In this respect, a top spot 27 of the cluster 25 controls by its reflectivity actuation of a switch 64 which determines whether any one or more resistors of a bank 65 are connected in series with either the bridge arm 55 or the bridge arm 59, depending on the position of the switch 64.

If all of the spots in the second cluster 52 were non-reflecting, then all of the resistors in the bank 65 would be connected in series with the bridge arm 55, with a fixed resistor 67 at the switch 64 then being connected in series with the bridge arm 59. Conversely, if all of the spots in the code cluster 52 were light-reflecting, then the fixed resistor 67 would be connected in series to the bridge arm 55, while all the resistors in the bank 65 would be shunted, whereby the bridge arm 59 would be directly connected to the negative signal output terminal 69. Between these extremes, there is a wide variety of combinations, available within the range of the second code cluster 52 for effecting a proper zero balancing operation on any transducer 12.

The same applies *mutatis mutandis* to the sensitivity adjustment effected in response to the third code cluster 53. In particular, that third code cluster controls the alternative switching of resistors from a third bank 71 across the excitation corners 72 and 73 or across the excitation diagonal of the Wheatstone bridge 15. This technique or method may be extended to also effect setting of additional resistors for thermal sensitivity compensation and other desired purposes.

Excitation or energization of the Wheatstone bridge 15 is supplied via power input terminals 74 and 75 and resistors 76 and 77 to the bridge corners 72 and 73. The photocells 37 read the code 26 via the optical fibers 38 in the cable 19 and actuate the drivers 48 and thereby the switches 43 to 46 accordingly, whereby the particular transducer 12 is automatically zero compensated, balanced and sensitivity adjusted. Any further temperature compensation, span normalization or other adjustment may be effected in the same manner.

Prior or after these adjustments, the transducer line 17 may be connected to a source of liquid or infusion container (not shown) and the catheter 16 may be flushed by depression of the button 21, whereby a larger flow path is established between the lines 17 and the catheter 16. The larger flow path is closed by a release of the button 21, and a blood pressure or other measurement or monitoring function may commence upon installation of the catheter in situ.

The pressure signal thereby produced by the Wheatstone bridge 15 proceeds via signal output terminals 69 and 79 shown in FIGS. 1 and 3 to the monitor 13, for display by a cathode ray tube or instrument 81 or for such other use as a given application may require.

Figure 4:
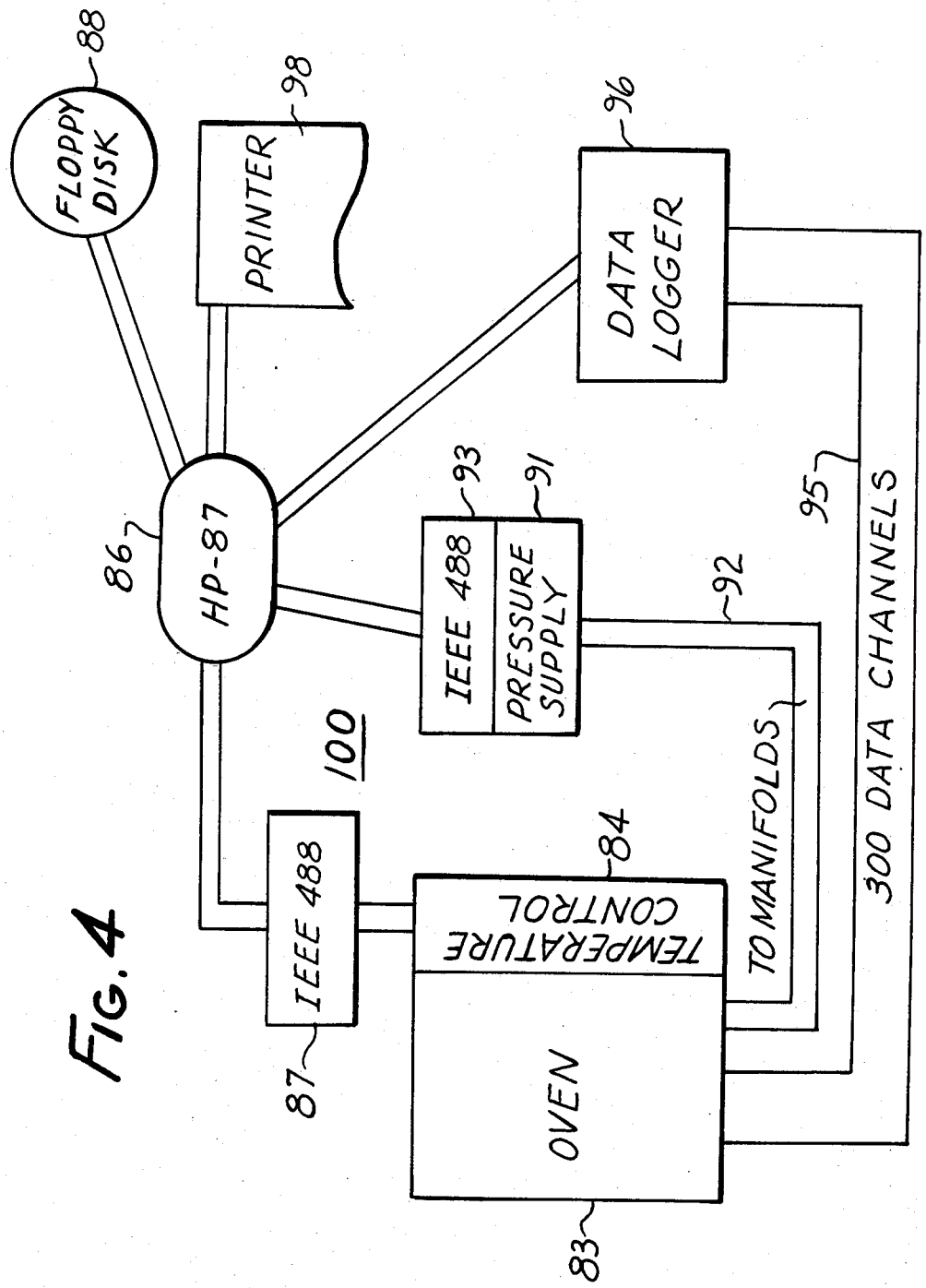
FIG. 4 is a block diagram of apparatus for providing records of transducer parameters, also according to an embodiment of the subject invention.

The resistors in the banks shown in FIG. 3 are preferably dimensioned on a binary weighted scale for most effective compensation, balancing and automatic adjustment. As shown in FIG. 4, provision of the binary code 26 for each transducer may be computerized.

In particular, FIG. 4 shows an oven 83 for receiving any transducer 12. This oven may, for instance, be of the Type 5900 by Delta Design Inc., of San Diego, California, having a Type V controller microprocessor 84 combined therewith for controlling the temperature to which the transducers in the oven are subjected.

A computer 86, which may be of the type HP-87, by Hewlet Packard, controls the microprocessor via an interface 87 which, for instance, may be of the Type IEEE 488. The computer 86 may, for instance, have a 128 K RAM memory, supplemented by a floppy disk 88.

The transducers in the oven 83 are subjected to pressure from pressure supply 91 connected via pressure lines 92 to manifolds of the oven 83. The pressure supply 91, which may include a pump and a reservoir, is controlled by the computer 86 via an interface 93 which, for instance, may be of the type IEEE 488. A suitable pressure supply 91 and interface 93 combination is manufactured by Ruska Instrument Corporation, of Houston, Texas. The transducers located in the oven 83 are connected by channels 95 to a data logger 96 which, for example, may be of the Type 3497 and which may be supplemented by an extender Type 3498, for instance.

The logger 96 logs the temperature and pressure output data of the transducers heated and pressurized in the oven 83. If desired, such logging may be in binary form, and the code 26 for each transducer 12 may be established therefrom. More conveniently, however, the data from the logger 96 are supplied to the computer 86 which calculates the code values and drives a printer 98 or other suitable peripheral for establishing an individual code 26 on a strip or disk 31 for each transducer 12. The codes thus provided are then individually applied to the respective transducers for reading by the photosensors 37 via optical fiber 38 in cable 19 in the field upon actual use of the particular transducer.

Reference may in this respect be had to FIGS. 1 to 3 and their above description.

It will thus be recognized that the subject invention from one aspect thereof, resides in methods and apparatus for operating a transducer 12 or other disposable apparatus and employs a computerized system 100 or other means and methods for determining parameters required for operation of the disposable apparatus and for providing a record 26 of such determined parameters on the apparatus 12. As explained with the aid of FIGS. 1 to 3, this aspect of the invention further provides a system 10 or other means and methods for machine-reading the parameters from the record 26 and for operating the apparatus with the aid of such machine-read parameters.

If the transducer 12 is made truly disposable, then repeated use thereof could endanger the accuracy of its operation, as well as the monitoring or measurement procedure itself. In this respect, conventional and reusable transducers are now routinely sterilized in hospitals and other institutions. Accordingly, there exists a risk that the disposable transducer 12 may be resterilized and reused as well.

Accordingly, pursuant to another aspect of the subject invention, the code or record 26 is rendered destructible by resterilization and the machine-reading thereof, as well as the operation of the transducer 12 or other disposable apparatus, is rendered impossible upon resterilization of such apparatus by destroying the code or record 26 by or upon resterilization.

According to a third aspect of the subject invention, the two main features so far disclosed are combined in methods and apparatus for operating the transducer 12 or other disposable apparatus subject to sterilization inimical to such disposable apparatus. The invention according to this aspect employs the system 100 or other means and methods for determining parameters required for operation of the apparatus and provides a record 26 of those determined parameters on the apparatus 12 itself. The invention according to this aspect further employs the system 10 or other means and methods for deriving the particular parameters by machine-reading, such as via the optical fibers 38 in the cable 19, in order to operate the apparatus as disclosed above in FIGS. 1 to 3, or in any other manner. According to this aspect of the invention, the record 26 is made destructible by resterilization and the machine-reading and the operation of the disposable apparatus 12 are rendered impossible upon resterilization of such apparatus by destroying the record 26 by such resterilization.

In FIG. 1 a box 102 symbolizes a sterilization process to which the transducer 12 is subjected, as indicated by an arrow 103. In this respect, a generally employed transducer sterilization procedure uses ethylene oxide gas. In that case, the code, markings and/or spots 26, 27 and 28 may be printed or provided with a dye with which ethylene oxide reacts so as to bleach or obliterate these markings or spots. For instance, the codes, markings or spots 26, 27 and 28 may be made of or comprise a dye including active amine and hydroxy groups or other active molecule sites. As examples, dyes of the aminoketone, hydroxyketone, quinoline, nitroso, cyanine or 7,7,8,8-tetracyanoquinodimethane type may be mentioned.

Another familiar type of sterilization uses high temperatures or pressurized steam. In practice, this may affect the structure or calibration of the transducer and thus its performance and the safety of persons depending thereon. Accordingly, in order to discourage resterilization of the transducer 12, the machine-readable code 26 or markings 27 or spots 28 may be printed or provided with an ink or dye that is bleached or otherwise rendered unreadable by heat or stream.

For instance, the code markings and/or spots 26, 27 and 28 may be printed or applied in the form of paraffin or another low-melting substance having a pigment or dye located therein and flowing off or being otherwise obliterated when subjected to the heat or steam of a sterilization process. Alternatively, a bleach or other agent obliterating a pigment or contrasting substance in the code, marking and/or spots 26, 27 and 28 may be microencapsulated in low-melting capsules, whereby the bleach or other obliterating agent is released upon exposure to the heat of the sterilization process.

In this or any equivalent manner, if a disposable transducer, such as the transducer 12 shown in FIG. 1, which is intended to be discarded after its first use, is nevertheless subjected to resterilization for reuse, then such resterilization process will obliterate the markings and/or spots 27 and 28, rendering the machine-readable code 26 unreadable. In consequence, the interfacing apparatus 14 will not be able to perform its compensation, balancing and sensitivity adjustment function on the particular transducer.

In practice, there are many situations in which only resterilization is to be thwarted, while sterilization prior to first use is highly desirable or even mandatory.

In this respect, FIG. 5 by way of example illustrates a preferred embodiment of the subject invention for allowing or providing for initial sterilization of the disposable apparatus or transducer 12 without impairment of a machine-readable code 26 (see FIG. 1) that has been rendered destructible by resterilization as herein disclosed or otherwise. In particular, the embodiment of FIG. 5 provides a cover or peelable label 126 removably located on the machine-readable record or code 26 or code disk 31 and protecting that code or the markings 27 and 28 against the effects of initial sterilization or sterilization before first use of the transducer 12. By way of example, if the code or markings 26, 27 or 28 are sensitized as mentioned above so as to be bleached or obliterated by ethylene oxide, then the cover or label 126 may be or include a non-porous membrane of a nylon, polyester, nylon or polyamide type which keeps the ethylene oxide away from the sensitized code 26.

The cover or label 126 may be of a pressure-sensitive or other peelable type, being releasably attached to the code disk 31 by an adhesive which is removed with the cover or label. Also, the sterilization-impervious cover or label 126 may have a projecting tab 127 for engagement by fingers of an operator or user. A crease line 128 may be provided across the cover or label to aid a removal thereof by tearing therealong, when the tab 127 is lifted or moved away from the transducer, as indicated by the dotted outline 129. Advantageously, a legend or instruction to the operator, such as "REMOVE BEFORE USE," may be printed or provided on the cover or label 126. The cover or label 126 is thus removed prior to the first use of the disposable apparatus or transducer, so that the machine-readable code 26 may thus be read by the apparatus 14 and will thereafter be destroyed by resterilization.

In practice, there are several ways in which the apparatus or operator can be told that the transducer 12 or other disposable apparatus has been subjected to an unauthorized or deleterious sterilization. For instance, if the code, markings and/or spots 26, 27 and 28 have been obliterated, then either none or all of the drivers 48 will be energized and either none or all of the switches 43 to 46 and 64 will be actuated. For instance, if the energization darkens all markings 27 and 28 so that no light is reflected through the optical fibers 38, then none of the drivers 48 is energized. On the other hand, if the undesired sterilization bleaches of the markings 27 and 28 so that light is reflected by each of them, then all of the drivers 48 are energized. In practice, this may be taken as the basis of an alarm condition, since some adjustment of transducer parameters is practically always acquired with the kind of disposable transducer 15 herein primarily contemplated.

By way of example, as indicated in FIG. 3 by a dotted line 105, all the outputs of the drivers 48 could be applied as inputs to a logic AND gate 106. Accordingly, if an unauthorized sterilization should bleach all the markings 27 and 28, so that all drivers 48 are energized, then all inputs of the AND gate 106 are energized as well, and such gate will supply an output along line 107 to an alarm indicator 108. Such indicator may then, for instance, supply a luminous or flashing indication that the particular transducer 12 or other disposable apparatus has been sterilized and should, therefore, not be used.

Alternatively or additionally, the apparatus may be disabled, such as by interrupting its energization or excitation. By way of example, FIG. 3 shows a line 109 going to a driver 110 and causing the same to open a switch 112, in order to interrupt the excitation, if the AND gate 106 indicates an alarm condition.

As customary in logic circuit design, the gate 106 may be realized by a combination of AND, NAND and/or NOR elements. For instance, if the pigments, dyes and/or bleaches employed for providing the markings 27 and 28 are such as to become dark upon sterilization, then a type of conventional gate may be used at 106 which provides an output upon none of the drivers 48 being energized. In that case, the alarm condition will occur at 108 and the energization be interrupted, such as 112, when none of the photocells 37 receives any light through their associated optical fibers 38.

Alternatively or additionally, there may be provided a further marking (not shown) located at 26 and assuming high reflectivity or strong opacity in response to sterilization, and being thus able to supply a signal, such as via an extra photocell 37 and extra fiber 38 (not shown) indicative of such undesired sterilization.

Various other modifications and variations within the spirit and scope of the subject invention and equivalents thereof will suggest themselves or become apparent to those skilled in the art from the subject extensive disclosure.

I claim:

1. In a method of operating a disposable apparatus subject to resterilization inimical to said disposable apparatus, the improvement comprising in combination the steps of:

determining parameters required for operation of said apparatus;

providing a record of said determined parameters on said apparatus;

deriving said parameters by machine-reading said record in order to operate said apparatus;

said record being made destructible by resterilization; and said machine-reading and the operation of said disposable apparatus being rendered impossible upon resterilization of said apparatus by destroying said record by said resterilization.

2. A method as claimed in claim 1, including the steps of:

providing said record in the form of a code combination on said apparatus;

machine-reading said code combination; and effecting parameter adjustments for said apparatus in response to said machine-read combination.

3. A method as claimed in claim 1, including the steps of:

subjecting said disposable apparatus to a physical influence affecting an output of said apparatus;

determining said parameters from said output;

providing a code combination indicative of said determined parameters; and providing said record by recording said code combination on said disposable apparatus.

4. A method as claimed in claim 1, including the step of:
providing for initial sterilization of said disposable apparatus without impairment of said record made destructible by resterilization.

5. A method as claimed in claim 1, including the steps of:
providing said record with a cover protecting said record against sterilization; and
removing said cover prior to first use of said apparatus.

6. In a method of operating a disposable apparatus including a transducing part, the improvement comprising in combination the steps of:
determining parameters required for operation of said transducing part of the apparatus;
providing a record of said determined parameters on said apparatus;
rendering said record destructible by resterilization;
machine-reading said parameters from said record;
operating said transducing part of the apparatus with the aid of said machine-read parameters; and
rendering said machine reading and the operation of said disposable apparatus impossible upon resterilization of said apparatus by destroying said record by said resterilization.

7. A method as claimed in claim 6, including the steps of:
providing said record in the form of a code combination on said apparatus;
machine-reading said code combination; and
effecting parameter adjustments for said apparatus in response to said machine-read code combination.

8. A method as claimed in claim 6, including the steps of:
subjecting said disposable apparatus to a physical influence affecting an output of said apparatus;
determining said parameters from said output;
providing a code combination indicative of said determined parameters; and
providing said record by recording said code combination on said disposable apparatus.

9. In a system for operating a disposable apparatus having parameters required for operation of said apparatus and being subject to resterilization inimical to said disposable apparatus,
the improvement comprising in combination:
a record of said parameters on said apparatus; and
means for machine reading said parameters from said record on said apparatus;
said record being destructible by sterilization, whereby said machine reading and the operation of said disposable apparatus are rendered impossible upon sterilization of said apparatus.

10. A system as claimed in claim 9, wherein:
said record comprises a code combination on said apparatus representing said parameters and being destructible by resterilization;
said machine-reading means include means for machine-reading said code combination; and
said system includes means connected to the latter machine-reading means for effecting parameter adjustments for said apparatus in response to said machine-read code combination.

11. A system as claimed in claim 9, including:
means for subjecting said disposable apparatus to a physical influence affecting an output of said apparatus;
means receiving said output for determining said parameters from said output;
means connected to said determining means for providing a code combination indicative of said determined parameters; and
means connected to said code combination providing means for recording said code combination in a manner destructible by resterilization on said disposable apparatus as said record.

12. A system as claimed in claim 9, including:
means for protecting said record against initial sterilization before first use of said apparatus.

13. A system as claimed in claim 9, including:
a cover means removably located on said record for protecting said record against initial sterilization before first use of said apparatus.

14. In a system for operating a disposable apparatus including a transducing part having parameters required for operation of said transducing part of the apparatus,
the improvement comprising in combination:
a record of said parameters on said apparatus;
means for machine-reading said parameters from said record; and
means connected to said machine-reading means for operating said transducing part of the apparatus with the aid of said machine-read parameters; wherein
said record is destructible by resterilization, whereby said machine reading and the operation of said disposable apparatus are rendered impossible upon resterilization of said apparatus.

15. A system as claimed in claim 14, wherein:
said record comprises a code combination on said apparatus representing said parameters;
said machine-reading means include means for machine-reading said code combination; and
said system includes means connected to the latter machine-reading means for effecting parameter adjustments for said transducing part of the apparatus in response to said machine-read code combination.

16. A system as claimed in claim 14, including:
means for subjecting said disposable apparatus to a physical influence affecting an output of said apparatus;
means for receiving said output for determining said parameters from said output;
means connected to said determining means for providing a code combination indicative of said determined parameters; and
means connected to said code combination providing means for recording said code combination on said disposable apparatus as said record.

17. A disposable apparatus including a transducing part having parameters required for operation of said transducing part of the apparatus, comprising:
a machine-readable record of said parameters required for operation of said transducing part on said apparatus;
said record being destructible by resterilization thereby rendering a machine-reading and operation of said disposable apparatus impossible upon resterilization of said apparatus.

18. A disposable apparatus as claimed in claim 17, wherein:
said record comprises a code combination on said apparatus representing said parameters, said code combination comprised in said record being machine-readable.

19. A disposable apparatus having parameters required for operation of said apparatus, comprising:
   a machine-readable record of said parameters on said apparatus;
   said record being destructible by resterilization; and
   means for protecting said record against initial sterilization before first use of said apparatus.

20. A disposable apparatus as claimed in claim 19, wherein:
   said record protecting means include a sterlization-impervious cover removably located on said record.

21. In a system for operating a disposable apparatus including a transducing part having parameters required for operation of said apparatus, the improvement comprising in combination:
   means for subjecting said disposable apparatus to a physical influence affecting an output of said transducing part of the apparatus;
   means for receiving said output for determining said parameters from said output;
   means connected to said determining means for providing a code combination indicative of said determined parameters; and
   means connected to said code combination providing means for providing a record of said code combination on said disposable apparatus;
   said record being destructible by sterilization, whereby said machine reading and the operation of said disposable apparatus are rendered impossible upon sterilization of said apparatus.

22. In a system for operating a disposable apparatus including a transducing part having parameters required for operation of said apparatus, the improvement comprising in combination:
   means for machine-reading said parameters from a record thereof on said apparatus; and
   means connected to said machine-reading means for effecting parameter adjustments for said transducing part of the disposable apparatus in response to said machine-read record;
   said record being destructible by sterilization, whereby said machine reading and the operation of said disposable apparatus are rendered impossible upon sterilization of said apparatus.

23. In a system for operating a disposable apparatus having parameters required for operation of said apparatus, the improvement comprising in combination:
   means for machine-reading said parameters from a record thereof on said apparatus including a cable including optical fibers forming part of said means for machine-reading said parameters from said record on the apparatus and including electrical wires as part of said means for effecting parameter adjustments for said disposable apparatus; and
   means connected to said machine-reading means for effecting parameter adjustments for said disposable apparatus in response to said machine-read record.

* * * * *